(12) United States Patent
Li et al.

(10) Patent No.: US 8,912,319 B2
(45) Date of Patent: Dec. 16, 2014

(54) SYNTHESIS OF 2'-DEOXY-2'-[$^{18}$F]FLUORO-5-METHYL-1-B-D-ARABINOFURANOSYLURACIL ($^{18}$F-FMAU)

(75) Inventors: Zibo Li, Logan, UT (US); Hancheng Cai, Troy, MI (US); Peter S. Conti, Pasadena, CA (US)

(73) Assignee: University of Southern California, Los Angeles, CA (US)

( * ) Notice: Subject to any disclaimer, the term of this patent is extended or adjusted under 35 U.S.C. 154(b) by 162 days.

(21) Appl. No.: 13/183,924

(22) Filed: Jul. 15, 2011

(65) Prior Publication Data

US 2012/0053337 A1    Mar. 1, 2012

Related U.S. Application Data

(60) Provisional application No. 61/364,728, filed on Jul. 15, 2010.

(51) Int. Cl.
*C07H 19/00* (2006.01)
*C07H 19/09* (2006.01)
*C07H 19/06* (2006.01)
*C07B 59/00* (2006.01)

(52) U.S. Cl.
CPC ............... *C07H 19/09* (2013.01); *C07H 19/06* (2013.01); *C07B 59/005* (2013.01)
USPC ................. 536/28.5; 536/28.52; 536/28.53; 536/28.54; 536/28.55

(58) Field of Classification Search
CPC ....... C07B 59/005; C07H 19/06; C07H 19/09
See application file for complete search history.

(56) References Cited

U.S. PATENT DOCUMENTS 5,879,661 A * 3/1999 Conti et al. ................... 424/1.81
6,331,287 B1 * 12/2001 Conti et al. ................... 424/1.89
6,683,045 B2 * 1/2004 Klecker et al. ...................... 514/1

OTHER PUBLICATIONS

PCT/US2011/044236 International Search Report dated Apr. 9, 2012; 4 pages.
Anderson et al. Improved synthesis of 2'-deoxy-2'-[18F]-fluoro-1-B-D-arabinofuranosyl-5-iodouracil ([18F]-FIAU). Nuclear Medicine and Biology (2010). 37:439-442.
Cai et al. The improved syntheses of 5-substituted 2'-[18F] fluoro-2'-deoxy-arabinofuranosyluracil derivatives {[18F] FAU, [18F]FEAU. [18F]FFAU. [18F] FCAU, [18F]FBAU and [18F]FIAU) using a mutlistep one-pot strategy. Nuclear Medicine and Biology (2011). 38:659-666.
Li et al. Improved synthesis of 2'-deoxy-2'-[18F] fluoro-5-methyl-1-B-D-arabinofuranosyluracil (18F-FMAU). The Journal of Nuclear Medicine. (2010). 51(Suppl 2): Abstract No. 533.
Li et al. Automated synthesis of 2'-deoxy-2'-[18F] fluoro-5-methyl-1-B-D-arabinofuranosyluracil ([18F]-FMAU) using a one reactor radiosynthesis module. Nuclear Medicine and Biology. (2011) 38:201-206.
Paolillo et al. A fully automated synthesis of [18F]-FEAU and [18F]-FMAU using a novel dual reactor radiosynthesis module. Journal of Labelled Compounds and Radiopharmaceuticals. (2009). 52(13):553-558.
Mangner et al. Synthesis of 2'-deoxy-2'-[18F] fluoro--D-arabinofuranosyl nucleosides, [18F]FAU, [18F]FMAU, [18F] FBAU and [18F]FIAU, as potential PET agents for imaging cellular proliferation. Nuclear Medicine and Biology (2003). 30:215-224.
Alauddin et al. Synthesis of [18F]-labeled 2'-deoxy-2'-fluoro-5-methyl-1-B-D-arabinofuranosyluracil ([18F]-FMAU). Journal of Labelled Compounds and Radiopharmaceuticals (2002). 45:583-590.
Alauddin et al. A general synthesis of 2'-deoxy-2'-[18F] fluoro-1-B-D-arabinofuranosyluracil and its 5-substituted nucleosides. Journal of Labelled Compounds and Radiopharmaceuticals (2003). 46:285-289.
Kappe et al. Controlled microwave heating in modern organic synthesis: highlights from the 2004-2008 literature. Mol Divers (2009). 13:71-193.
Santagada et al. Microwave Assisted Synthesis: A New Technology in Drug Discovery. Mini-Reviews in Medicinal Chemistry (2009). 9:340-358.
Stone-Elander et al. Microwaving in F-18 Chemistry: Quirks and Tweaks. Ernst Schering Res Found Workshop (2007). pp. 243-269.
Elizarov et al. Design and Optimization of Coin-Shaped Microreactor Chips for PET Radiopharmaceutical Synthesis. The Journal of Nuclear Medicine (2010). 51(2): 282-287.
Duffy et al. Rapid Prototyping of Microfluidic Systems in Poly(dimethylsiloxane). Anal. Chem. (1998). 70(23): 4974-4984.

* cited by examiner

*Primary Examiner* — Lawrence E Crane
(74) *Attorney, Agent, or Firm* — Linda B. Huber; Nixon Peabody LLP

(57) ABSTRACT

The present invention relates to methods of synthesizing $^{18}$F-FMAU. In particular, $^{18}$F-FMAU is synthesized using one-pot reaction conditions in the presence of Friedel-Crafts catalysts. The one-pot reaction conditions are incorporated into a fully automated cGMP-compliant radiosynthesis module, which results in a reduction in synthesis time and simplifies reaction conditions. The one-pot reaction conditions are also suitable for the production of 5-substituted thymidine or cytidine analogs. The products from the one-pot reaction (e.g. the labeled thymidine or cytidine analogs) can be used as probes for imaging tumor proliferative activity. More specifically, these [$^{18}$F]-labeled thymidine or cytidine analogs can be used as a PET tracer for certain medical conditions, including, but not limited to, cancer disease, autoimmunity inflammation, and bone marrow transplant.

7 Claims, 5 Drawing Sheets

SYNTHESIS OF 2'-DEOXY-2'-[$^{18}$F]FLUORO-5-METHYL-1-B-D-ARABINOFURANOSYLURACIL ($^{18}$F-FMAU)

CROSS-REFERENCE TO RELATED APPLICATIONS

This application claims the benefit of priority to U.S. Provisional Patent Application Ser. No. 61/364,728 filed Jul. 15, 2010, incorporated by reference herein in its entirety.

STATEMENT REGARDING FEDERALLY-SPONSORED RESEARCH

This invention was made with government support under contract No. DE-SC0002353 awarded by the Department of Energy. The U.S. Government may have certain rights in this invention.

FIELD OF INVENTION

This invention relates to the synthesis of $^{18}$F-FMAU. More specifically, the invention provides a method for the synthesis of $^{18}$F-FMAU, using one-pot reaction conditions. The one-pot synthesis conditions can be incorporated into a fully automated Current Good Manufacturing Practice-compliant (cGMP-compliant) radiosynthesis system.

BACKGROUND

A number of radiolabeled 2'-deoxy-2'-fluoro-5-substituted-1-β-D-arabinofuranosyl-uracil and -cytosine derivatives have been recognized as efficient probes for imaging tumor proliferative activity and HSV1-tk reporter gene expression with positron emission tomography (PET). Among these, 2'-deoxy-2'-[$^{18}$F]fluoro-5-methyl-1-β-D-arabinofuranosyl-uracil ([$^{18}$F]-FMAU), 2'-deoxy-2'-fluoro-5-[$^{11}$C]methyl-1-β-D-arabinofuranosyl-uracil ([$^{11}$C]-FMAU) and 2'-deoxy-2'-[$^{18}$F]fluoro-5-bromo-1-β-D-arabinofuranosyl-uracil ([$^{18}$F]-FBAU) are markers for DNA synthesis through phosphorylation by human and other mammalian nucleoside kinases including thymidine kinase TK1 and TK2, and FMAU is currently undergoing clinical studies in multiple centers for imaging tumor proliferation in a variety of cancer types and DNA synthesis. The other derivatives, such as 2'-deoxy-2'-[$^{18}$F]-fluoro-5-iodo-1-β-D-arabinofuranosyl-uracil ([$^{18}$F]-FIAU), 2'-deoxy-2'-[$^{18}$F]fluoro-5-fluoro-1-β-D-arabinofuranosyl-uracil ([$^{18}$F]-FFAU) and 2'-deoxy-2'-[$^{18}$F]-fluoro-5-chloro-1-β-D-arabinofuranosyl-uracil ([$^{18}$F]-FCAU) are excellent substrates for the viral kinases such as herpes simplex virus (HSV) type 1 and 2, and FIAU is also a substrate for hepatitis B-virus and Epstein B virus (EBV) thymidine kinase. These 2'-fluoro-5-substituted arabinosyluracil derivatives were synthesized and evaluated earlier as antiviral agents. Recently, $^{18}$F-1-(2'-deoxy-2'-fluoro-arabinofuranosyl)cytosine ($^{18}$F-FAC), 2'-deoxy-2'-$^{18}$F-fluoro-5-methyl-beta-L-arabinofuranosylcytosine ($^{18}$F-FMAC) and their analogs have been shown to be potential PET tracer for cancer disease, autoimmunity inflammation, and bone marrow transplant. The first radiochemical synthesis of FMAU with PET isotope ([$^{11}$C]) was reported by the applicants. However, due to the short half-life of [$^{11}$C]($t_{1/2}$=20 min), the applicants developed the radiosynthesis of [$^{18}$F]-labeled FMAU and other 5-substituted thymidine analogues. After this synthesis was disclosed, another group of investigators also reported the [$^{18}$F]-labeled synthesis of these pyrimidine nucleoside analogues.

The radiosynthesis of F-18 FMAU (Scheme 1) involves radiofluorination of 2-trifluoromethane-sulfonyl-1,3,5-tri-O-benzoyl ribofuranose to 2-[$^{18}$F]-fluoro-1,3,5-tri-Obenzoyl arabinofuranose derivative, followed by conversion to 1-bromo-2-[$^{18}$F]-fluoro-1,3,5-tri-O-benzoyl derivative, then coupling of the 1-bromo-2-[$^{18}$F]-fluoro-2,3,-di-O-benzoylarabinofuranose with 2,4-bis-trimethylsilyluracil derivatives. Finally, hydrolysis of the protecting groups from the sugar moiety and HPLC purification produces the desired products. Specific reaction conditions and reagents used are detailed in Scheme 1.

An ideal radiosynthesis procedure involves a single step radiolabeling of a precursor compound, followed by hydrolysis of protecting groups, if necessary, and purification of the crude mixture. However, such an ideal method has not been successful when applied to the radiolabeling of 2'-fluoroarabinosubstituted pyrimidine nucleosides. Multiple steps are required after radiolabeling of the sugar moiety.

Scheme 1. Multistep synthesis of $^{18}$F-FMAU

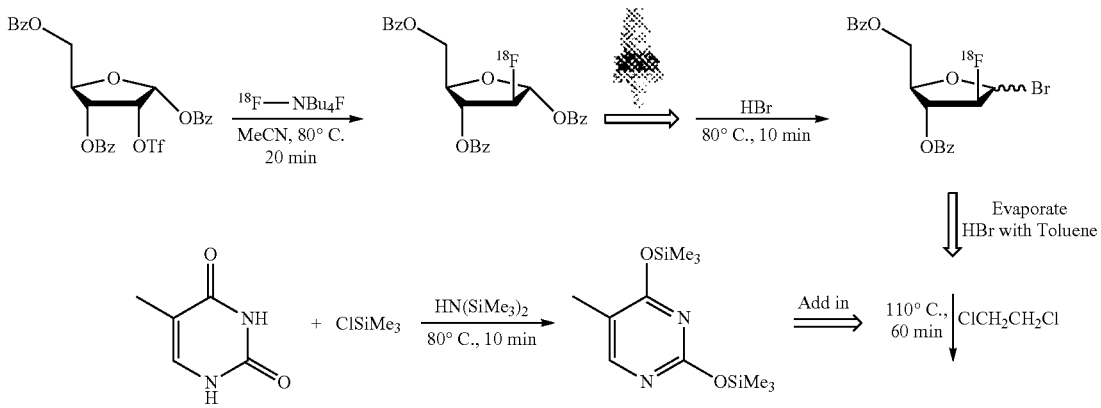

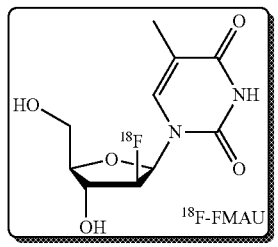

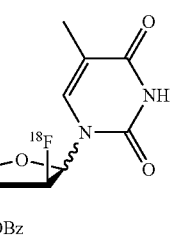

i) NaOMe, MeOH, 80° C.
ii) HPLC purification

Although the applicants and other researchers in the field have demonstrated these reactions are very reliable and reproducible, the complexity of this method often requires significant modification of existing commercial automated modules, accompanied by frequent production failures. In order to find an efficient fully automated Current Good Manufacturing Practice-compliant (cGMP-compliant) radiosynthesis system for the production of these probes, the applicants have been optimizing the reaction conditions to reduce synthetic time and simplify reaction conditions. Recently, the applicants reported the use of Friedel-Crafts catalysts for a synthesis of $^{18}$F-FMAU, which also includes a significantly simplified one-pot reaction condition (see below). However, a need exists for the fully automated synthesis of [$^{18}$F]-FMAU using one pot reaction conditions. According to certain embodiments, the method is compatible with most commercially available modules typically used for production of cGMP compliant radiotracers for clinical applications.

One-pot synthesis of $^{18}$F-FMAU

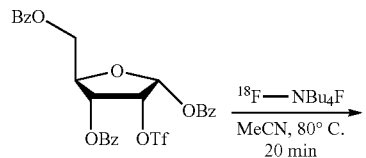

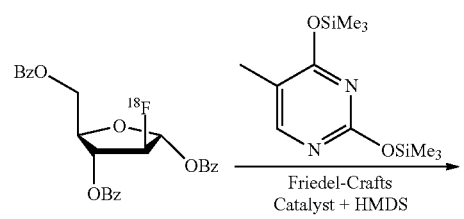

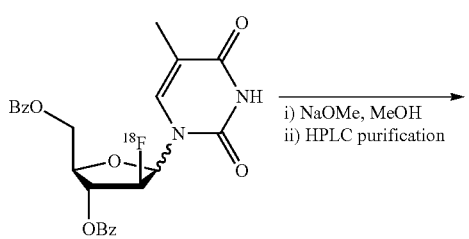

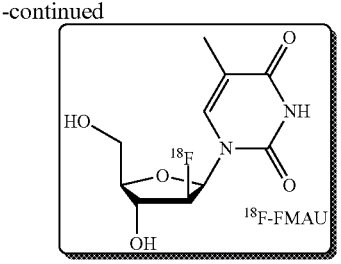

SUMMARY OF THE INVENTION

In one embodiment, the invention relates to compositions and methods of synthesizing 2'-deoxy-2'-[$^{18}$F]-fluoro-5-substituted-1-β-D-arabinofuranosyl-uracil and -cytosine compounds in a one-pot reaction. The method comprises radiolabeling a precursor sugar with $^{18}$F, contacting the $^{18}$F radiolabeled sugar with a silylated uracil or -cytosine in the presence of a Friedel-Crafts catalyst and hexamethyldisilazane (HMDS), incubating the components in the previous step under conditions which allow for conjugation of the $^{18}$F radiolabeled sugar and the silylated uracil or -cytosine, hydrolyzing the protecting groups of the components in step and purifying the hydrolyzed product. The synthesis may take place in a fully automated cGMP-compliant radiosynthesis module.

In a related embodiment, the invention relates to compositions and methods of synthesizing [$^{18}$F]-labeled thymidine and cytidine analogues in a one-pot reaction. The method comprises radiolabeling of a precursor sugar with $^{18}$F, contacting the $^{18}$F radiolabeled sugar with a silylated uracil or cytosine derivatives in the presence of a Friedel-Crafts catalyst and HMDS, incubating the components in the previous step under conditions which allow for conjugation of the $^{18}$F radiolabeled sugar and the silylated uracil or cytosine derivatives, hydrolyzing the protecting groups of the components in the previous step and purifying the hydrolyzed product.

According to certain embodiments, the invention additionally relates to methods of using the [$^{18}$F]-labeled thymidine or cytidine analogue produced in a one-pot reaction. The one-pot synthesis includes radiolabeling of a precursor sugar with $^{18}$F, contacting the $^{18}$F radiolabeled sugar with a silylated uracil or cytosine derivatives in the presence of a Friedel-Crafts catalyst and HMDS, incubating the components in the previous step under conditions which allow for conjugation of the $^{18}$F radiolabeled sugar and the silylated uracil or cytosine derivatives, hydrolyzing the protecting groups of the components in the previous step and purifying the hydrolyzed product. The method of using comprises utilizing the [$^{18}$F]-labeled thymidine or cytidine analogue produced in a one-pot reaction as a probe for imaging tumor proliferative activity.

These [$^{18}$F]-labeled thymidine or cytidine analogue can be used as a PET tracer for certain medical conditions, including, but not limited to, cancer disease, autoimmunity inflammation, and bone marrow transplant.

The above-mentioned and other features of this invention and the manner of obtaining and using them will become more apparent, and will be best understood, by reference to the following description, taken in conjunction with the accompanying drawings. The drawings depict only typical embodiments of the invention and do not therefore limit its scope.

Figure 1:
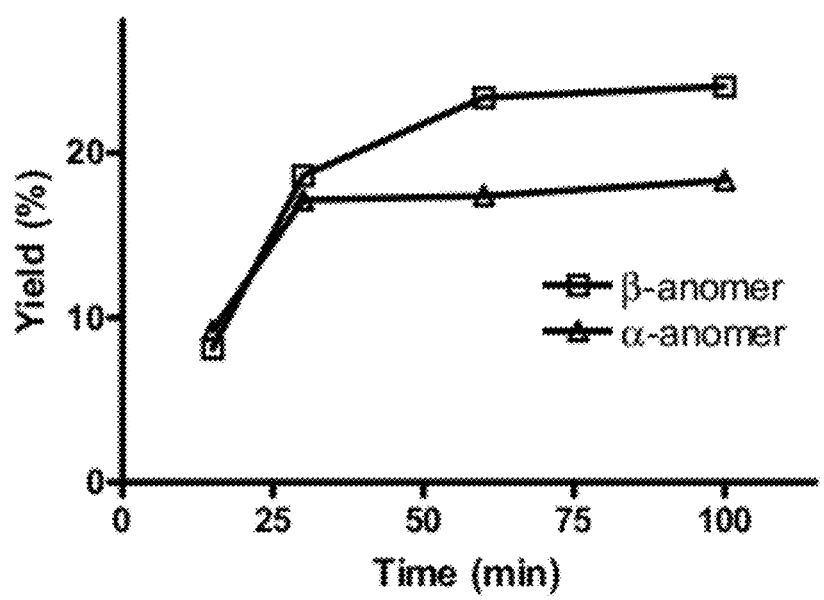
FIG. 1 is a graph of the conjunction yield for TMSOTf catalyzed FMAU synthesis as a function of time.

DESCRIPTION OF THE INVENTION $^{18}$F-FMAU is an established PET probe used to monitor cellular proliferation. The current radiosynthesis of $^{18}$F-FMAU requires multiple steps, including the HBr activation of the sugar prior to the coupling with silylated uracil. This multiple step procedure makes the development of an automated protocol difficult and complicated. Thus, fully automated cGMP-compliant radiosynthesis modules for the synthesis of $^{18}$F-FMAU are necessary for clinical applications.

The present invention provides a one-pot reaction condition for the synthesis of $^{18}$F-FMAU, which eliminates the need for a bromination step. The one-pot reaction synthesis uses Friedel-Crafts catalysts to simplify reaction conditions and reduce the synthesis time. In addition, the present invention provides methods for the use of the one-pot reaction synthesis in a fully automated cGMP-compliant radiosynthesis module.

Further, the applicants have provided a method for the one-pot synthesis of [$^{18}$F]-FMAU that produces high yields and high purity using a one-reactor synthesis module. The simplified and reliable synthetic method can be widely applied for the production of other 2'-[$^{18}$F]fluoro-2'-deoxy-arabino-5-substituted pyrimidine nucleoside analogues, thus making them more accessible for preclinical and clinical research and diagnostics. According to certain embodiments, these pyrimidine nucleoside analogues include, but are not limited to, 2'-fluoro-5-ethyl-1-β-D-arabinofuranosyluracil (FEAU), 2'-Deoxy-2'-fluoro-5-fluoro-1-β-D-arabinofuranosyluracil (FFAU), 1-(2-deoxy-2-fluoro-β-D-arabinofuranosyl)-5-chlorouracil (FCAU), 1-(2-deoxy-2-fluoro-β-D-arabinofuranosyl)-5-bromouracil (FBAU), 1-(2-deoxy-2-fluoro-β-D-arabinofuranosyl) uracil (FAU), 2'-fluoro-2'-deoxy-1-β-D-arabinofuranosyl-5-iodouracil (FIAU), 1-(2-deoxy-2-fluoro-β-D-arabinofuranosyl) cytosine (FAC), 2'-deoxy-2'-fluoro-5-methyl-1-β-D-arabinofuranosylcytosine (FMAC), 2'-fluoro-5-ethyl-1-β-D-arabinofuranosylcytosine (FEAC), 2'-Deoxy-2'-fluoro-5-fluoro-1-β-D-arabinofuranosyluracil (FFAC), 1-(2-deoxy-2-fluoro-β-D-arabinofuranosyl)-5-chlorocytosine (FCAC), 1-(2-deoxy-2-fluoro-β-D-arabinofuranosyl)-5-bromocytosine (FBAC), and 2'-deoxy-2'-fluoro-5-hydroxymethyl-1-β-D-arabinofuranosylcytosine (FHMAC).

According to certain embodiments, the invention additionally relates to methods of using the [$^{18}$F]-labeled thymidine or cytidine analogue produced in a one-pot reaction. The one-pot synthesis includes radiolabeling of a precursor sugar with $^{18}$F, contacting the $^{18}$F radiolabeled sugar with a silylated uracil or cytosine derivatives in the presence of a Friedel-Crafts catalyst and HMDS, incubating the components in the previous step under conditions which allow for conjugation of the $^{18}$F radiolabeled sugar and the silylated uracil or cytosine derivatives, hydrolyzing the protecting groups of the components in the previous step and purifying the hydrolyzed product. The method of using comprises utilizing the [$^{18}$F]-labeled thymidine or cytidine analogue produced in a one-pot reaction as a probe for imaging tumor proliferative activity. These [$^{18}$F]-labeled thymidine or cytidine analogue can be used as a PET tracer for certain medical conditions, including, but not limited to, cancer disease, autoimmunity inflammation, and bone marrow transplant.

EXAMPLES

Example 1

Reagents and Instrumentation

All reagents and solvents were purchased from Aldrich Chemical Co. (Milwaukee, Wis.), and used without further purification. Solid phase extraction cartridges (silica gel, 900 mg) were purchased from Waters. Ion exchange cartridges were purchased from ABX (Germany). 2-Trifluoromethanesulfonyl-1,3,5-tri-O-benzoyl-α-D-ribofuranose (precursor) and bis-2,4-trimethylsilyl-5-methyluracil were prepared in house or purchased from ABX (Germany). Non-radioactive compounds FMAU was prepared in house for HPLC standards. High performance liquid chromatography (HPLC) was performed on a pump (integrated with the synthesis module) with UV detector operated at 254 nm, and a built in radioactivity detector (GE Healthcare, Germany) using a semi-preparative C18 reverse phase column (G.E Health care, 16×250 mm, Germany) and an analytical C18 column (Alltech, 4.6×250 mm, (Deerfield, Ill.)). A solution of 6% ethanol in aqueous $Na_2HPO_4$ (20 mM, pH 6.5) was used for purification of [$^{18}$F]-FMAU. A solution of 8% MeCN in water was used for quality control analysis of [$^{18}$F]-FMAU on analytical HPLC.

Example 2

Reduction of the Conjugation Time

Previously, the applicants conjugated 2,4-bis-trimethylsilyl-5-methyluracil to a fluorinated bromo-sugar at 100° C. for 60 mins. The initial attempt focused on the feasibility of reducing reaction time by introducing a catalyst. Friedel-Crafts catalysts have been widely used for the synthesis of nucleosides. Trimethylsilyl trifluoromethanesulfonate (TMSOTf) shows the properties of strong Lewis acid and is suitable as Friedel-Crafts catalyst. The overall synthetic strategy is given in Scheme 2.

Scheme 2.

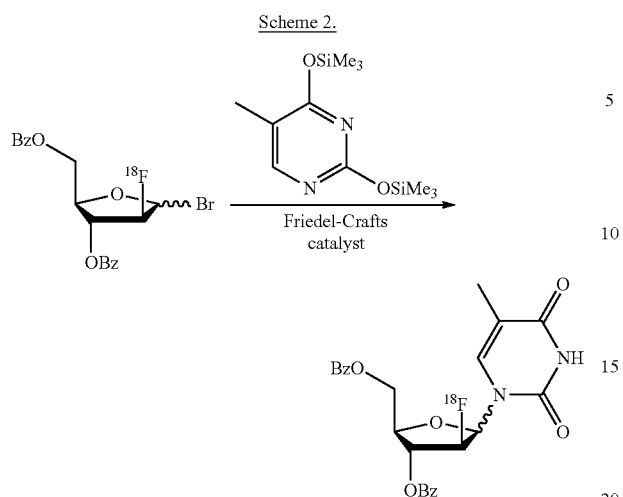

More specifically, 1-bromo-2-[$^{18}$F]fluoro-2,3,-di-O-benzoylarabinofuranose was prepared as reported. After the solvent was evaporated, 20 mg of 2,4-bis-trimethylsilyl-5-methyluracil containing TMSOTf was added to the V-vial and heated at different temperatures. The crude mixture is hydrolyzed using standard procedures and analyzed with HPLC.

As shown in Table 1, at 80° C., the β-anomer (desired FMAU product) yield increased from 22.2% to 50.1% when the reaction time was increased to 60 min from 15 min (Table 1, entry 1-3). Compared with old method, there is no significant advantage except the decreased reaction temperature. However, at 100° C., the yield for β-anomer could reach 50.1% within 15 min in the presence of TMSOTf (Table 1, Entry 4). Extending the reaction time to 60 min at this temperature only slightly increase the conjugation yield (Table 1, Entry 5). In conclusion, the presence of TMSOTf could significantly reduce the reaction time needed for the conjugation.

TABLE 1

TMSOTf catalyzed conjugation between 2,4-bis-trimethylsilyl-5-methyluracil and 1-bromo-2-[$^{18}$F]-fluoro-1,3,5-tri-O-benzoyl derivative.

| Entry | TMSOTf | Temperature | Time | α-anomer | β-anomer |
|---|---|---|---|---|---|
| 1 | 100 μL | 85° C. | 15 min | 17.6 | 22.2 |
| 2 | 100 μL | 85° C. | 30 min | 20.6 | 34.2 |
| 3 | 100 μL | 85° C. | 60 min | 23.1 | 50.1 |
| 4 | 100 μL | 100° C. | 15 min | 12.1 | 55.0 |
| 5 | 100 μL | 100° C. | 60 min | 13.0 | 67.0 |

The labeling yield was calculated based on HPLC results.

Example 3

Simplified FMAU Synthesis with Friedel-Crafts Catalysts

Although the applicants have successfully demonstrated that the sugar-base reaction time could be reduced to 15 min, the complexity of the reaction still makes it hard to be incorporated into an automated box. As the Friedel-Crafts catalysts have been successfully applied to catalyze the glycosidations of silyated methyluracils, the applicants also investigated the feasibility of synthesizing FMAU without the bromination step. Originally, the applicants tried to develop a one pot method using similar conditions as the well established cold reaction (Scheme 3). However, no desired product was observed. The only difference between the hot condition and the cold condition was the presence of carbonate or bicarbonate base that was carried over from the fluorination step.

Scheme 3

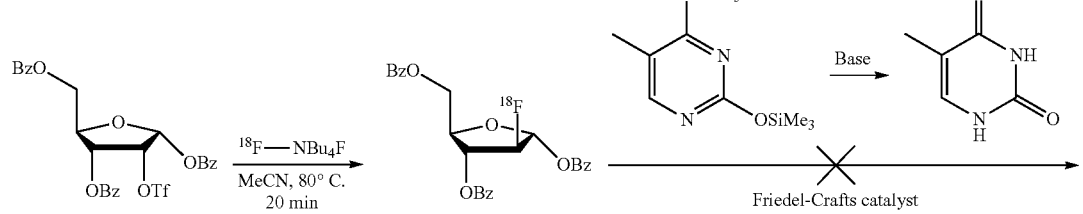

In order to test whether this carbonate or bicarbonate base can deprotect the 2,4-bis-trimethylsilyl-5-methyluracil and make it less reactive, the crude mixture of fluorinated sugar was passed through a silica cartridge to remove the inorganic base (Scheme 4). As expected, [$^{18}$F]-FMAU was successfully obtained in the presence of the TMSOTf Friedel-Crafts catalyst. The reaction was performed at different conditions and the results summarized in Table 2. Specifically, 2-[$^{18}$F]fluoro-2,3,-di-O-benzoylarabinofuranose was prepared as reported. The reaction crude mixture was then passed through a silica cartridge and washed into the reactor with 2 mL EtOAc. After the solvent was evaporated, 20 mg of 2,4-bis-trimethylsilyl-5-methyluracil containing TMSOTf was added and heated at different temperatures. The crude mixture was then hydrolyzed using standard procedures and analyzed with HPLC.

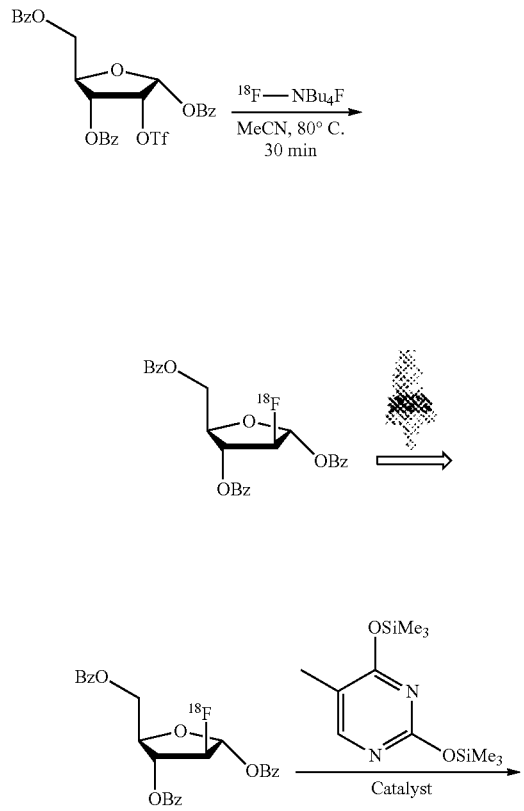

Scheme 4. Multistep synthesis of $^{18}$F-FMAU

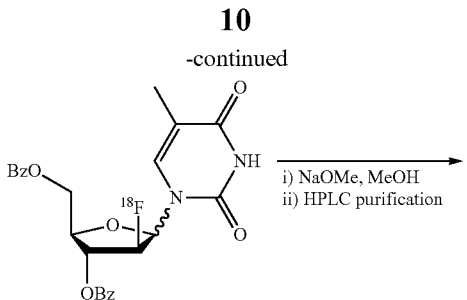

Freshly prepared silylated uracil did not give higher yield compared with a commercially available one (Table 2, entry 1-2). Decreasing the catalyst amount to 40 µL increased the α/β-anomer selectivity, but only slightly increased the labeling yield (Table 2, entry 3). Changing the solvent to acetonitrile increased the α/β-anomer selectivity, but the labeling yield was decreased to 14.2% (Table 2, entry 4). THF provided comparable reasonable α/β-anomer selectivity and labeling yield (Table 2, entry 5). Changing the solvent to DMF or DMSO did not provide the desired product when the reaction was performed at 85° C. and 145° C. (Table 2, entry 6-9).

TABLE 2

TMSOTf catalyzed conjugation between 2,4-bis-trimethylsilyl-5-methyluracil and-[$^{18}$F]fluoro-2,3,-di-O-benzoylarabinofuranose after passing silica cartridge.

| Entry | solvent | silylated uracil | TMSOTf | Temperature | Time | α-anomer | β-anomer |
|---|---|---|---|---|---|---|---|
| 1 | (CH$_2$Cl)$_2$ | 20 mg* | 200 µL | 85° C. | 60 min | 35.4 | 34.3 |
| 2 | (CH$_2$Cl)$_2$ | 20 mg | 200 µL | 85° C. | 60 min | 42.6 | 40.1 |
| 3 | (CH$_2$Cl)$_2$ | 20 mg | 40 µL | 85° C. | 60 min | 4.1 | 47.8 |
| 4 | ACN | 20 mg | 200 µL | 85° C. | 60 min | 2.0 | 14.2 |
| 5 | THF | 20 mg | 200 µL | 85° C. | 60 min | 9.2 | 38.9 |
| 6 | DMF | 20 mg | 200 µL | 85° C. | 60 min | N | N |
| 7 | DMSO | 20 mg | 200 µL | 85° C. | 60 min | N | N |
| 8 | DMF | 20 mg | 200 µL | 145° C. | 60 min | N | N |
| 9 | DMSO | 20 mg | 200 µL | 145° C. | 60 min | N | N |

The labeling yield was calculated based on HPLC results.
*Freshly synthesized precursor.

As demonstrated above, the presence of a Friedel-Crafts catalyst can successfully eliminate the bromination step that would otherwise be required for FMAU synthesis. The β anomer can also be favorably obtained. Although it is not a one pot reaction method, this labeling condition has been greatly simplified and is compatible with a commonly used one reactor module.

Example 4

Development of the One POT Procedure

An ideal radiosynthesis procedure involves a single step radiolabeling of a precursor compound, followed by hydrolysis of protecting groups, and if necessary, purification of the crude mixture. In order to further simplify the reaction conditions, the applicants developed a one pot synthesis procedure for FMAU production. As the residue base deprotected 2,4-bis-trimethylsilyl-5-methyluracil, HMDS was added to the mixture so that the trimethylsilyl groups would be added to the decomposed 5-methyluracil (Scheme 5). Specifically, 2-[$^{18}$F]fluoro-2,3,-di-O-benzoylarabinofuranose was prepared as reported After the solvent was evaporated, 20 mg of 2,4-bis-trimethylsilyl-5-methyluracil containing TMSOTf and HMDS were added and heated at different temperatures. The crude mixture was hydrolyzed using standard procedures and analyzed with HPLC.

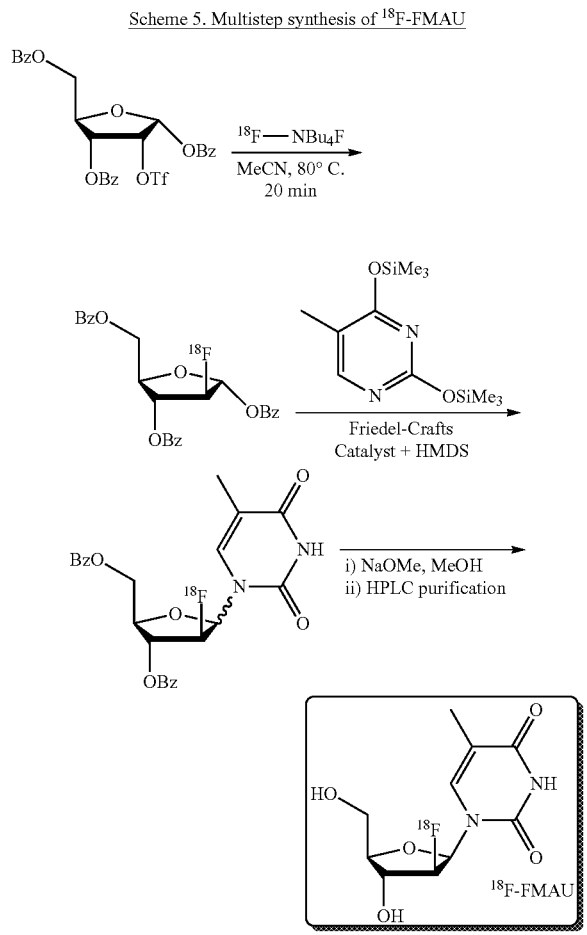

Scheme 5. Multistep synthesis of $^{18}$F-FMAU

FMAU was synthesized by the reaction of 2-deoxy-2-[$^{18}$F]fluoro-1,3,5-tri-O-benzoyl-D-arabinofuranose ($^{18}$F-sugar) and bis-2,4-(trimethylsilyloxy)-5-methyluracil (silylated uracil) in the presence of various Friedel-Crafts catalysts. Passing the $^{18}$F-sugar through a silica cartridge before the coupling reaction improved the FMAU specific activity to 1,500 mCi/μmol, increased the α/β anomer ratio to 1:4, and eliminated the need for HMDS. Although it is not one pot, this labeling condition is still compatible with the commonly used one reactor module. Various reaction temperatures, times, solvents, and additives, were also explored to optimize the reaction.

Friedel-Crafts Catalysts

Out of the four Friedel-Crafts catalysts tested (AlCl$_3$, SnCl$_4$, ZnCl$_2$, and TMSOTf), TMSOTf was found to be most efficient. The conjugation yield for TMSOTf catalyzed FMAU synthesis is 46.8% starting from fluorinated sugar based on HPLC analysis (Table 3, entry 1). The yields of the synthesis using others catalysts (AlCl$_3$, SnCl$_4$, ZnCl$_2$) were too low to be detected (Table 3, entry 2-5).

The Amount of TMSOTf

The amount of TMSOTf was found to affect reaction yield and selectivity. The applicants added 20 μL, 50 μL, 100 μL, and 200 μL TMSOTf to the reaction and kept other conditions unchanged (temperature: 85° C., protected base 20 mg, HMDS 100 μL, solvent 300 μL CH$_2$Cl—CH$_2$Cl). All of the tested conditions lead to FMAU product, but the amount of catalyst affected the reaction yield and selectivity (Table 3, entry 1, 6-8). If the amount of TMSOTf was lower than 20 μL, the labeling yield was significantly decreased. The labeling yield was increased to 26.5%, 46.8%, 47.4% with 50 μL, 100 μL, and 200 μL TMSOTf respectively.

Hexamethyldisilazane (HMDS).

HMDS was necessary for the one-pot conjugation, otherwise the yield was too low to be detected if the reaction was performed without HMDS (Table 3, entry 9).

Solvent Effect.

The effect of the solvent used was tested by keeping all parameters constant (TMSOTf (100 μL), 85° C., protected base 20 mg, HMDS (100 μL), tested solvent (300 μL)). Solvents were found to have a significant effect on the conjugation yield. Of the solvents tested, CH$_2$Cl—CH$_2$Cl (dichloroethane), acetonitrile, and THF all produced a final product with dichloroethane giving the highest yield (Table 3, entry 1, 12, and 13). Since acetonitrile could lower the labeling yield as compared to dichloroethane, it may be advantageous for it to be evaporated after the fluorination step when used in automation. Likewise, DMSO, DMF, or DMSO/DMF doped dichloroethane lead to significantly decreased conjugation yield (Table 3, entry 14-20).

Moreover, the applicants discovered that TMSOTf does not only act as a catalyst, but also as a co-solvent. During the old synthesis, the uracil reactant was difficult to dissolve in dichloroethane, and had to be added to the reaction mixture as a suspension. In the presence of TMSOTf, this uracil reagent can easily form a homogenous solution, which not only helps the coupling reaction, but also allows for easier atomization.

Reaction Time.

As shown in FIG. 1, the catalyzed conjugation was also analyzed at different time points (15, 30, 60, and 100 min). The applicants discovered that the labeling yield reaches a plateau after 60 min (Table 3, entry 21-24).

TABLE 3

Conjugation between 2,4-bis-trimethylsilyl-5-methyluracil and-[$^{18}$F]fluoro-2,3,-di-O-benzoylarabinofuranose without passing silica cartridge.

| Entry | solvent | silylated uracil | Catalyst | T (° C.) | Time | α-anomer | β-anomer |
|---|---|---|---|---|---|---|---|
| 1 | (CH$_2$Cl)$_2$ | 20 mg | TMSOTf (100 μL) + HMDS (100 μL) | 85 | 60 min | 40.4 | 46.8 |
| 2 | (CH$_2$Cl)$_2$ | 20 mg | ZnCl$_2$ (150 mg) + HMDS (100 μL) | 85 | 60 min | N | N |
| 3 | (CH$_2$Cl)$_2$ | 20 mg | AlCl$_3$ (160 mg) + HMDS (100 μL) | 85 | 60 min | N | N |
| 4 | (CH$_2$Cl)$_2$ | 20 mg | SnCl$_4$ (130 μL) + HMDS (100 μL) | 85 | 60 min | N | N |
| 5 | (CH$_2$Cl)$_2$ | 20 mg | SnCl$_4$ (130 μL) + HMDS (100 μL) | 120 | 60 min | N | N |
| 6 | (CH$_2$Cl)$_2$ | 20 mg | TMSOTf (20 μL) + HMDS (100 μL) | 85 | 60 min | low | <5 |
| 7 | (CH$_2$Cl)$_2$ | 20 mg | TMSOTf (50 μL) + HMDS (100 μL) | 85 | 60 min | 22.4 | 26.5 |
| 8 | (CH$_2$Cl)$_2$ | 20 mg | TMSOTf (200 μL) + HMDS (100 μL) | 85 | 60 min | 44.8 | 47.4 |
| 9 | (CH$_2$Cl)$_2$ | 20 mg | TMSOTf (100 μL) | 85 | 60 min | N | N |
| 10 | (CH$_2$Cl)$_2$ | 20 mg* | TMSOTf (200 μL) + HMDS (100 μL) | 85 | 60 min | 31.8 | 32.1 |
| 11 | (CH$_2$Cl)$_2$ | 10 mg# | TMSOTf (200 μL) + HMDS (100 μL) | 85 | 60 min | 26.8 | 27.0 |
| 12 | ACN | 20 mg | TMSOTf (100 μL) + HMDS (100 μL) | 85 | 60 min | 18.7 | 19.1 |
| 13 | THF | 20 mg | TMSOTf (100 μL) + HMDS (100 μL) | 85 | 60 min | 9 | 34.9 |
| 14 | DMSO | 20 mg | TMSOTf (100 μL) + HMDS (100 μL) | 85 | 60 min | N | N |
| 15 | DMF | 20 mg | TMSOTf (100 μL) + HMDS (100 μL) | 85 | 60 min | N | N |
| 16 | (CH$_2$Cl)$_2$/DMSO (10%) | 20 mg | TMSOTf (100 μL) + HMDS (100 μL) | 85 | 60 min | N | N |
| 17 | (CH$_2$Cl)$_2$/DMF (10%) | 20 mg | TMSOTf (100 μL) + HMDS (100 μL) | 85 | 60 min | N | N |
| 18 | (CH$_2$Cl)$_2$/DMSO (1%) | 20 mg | TMSOTf (100 μL) + HMDS (100 μL) | 85 | 60 min | 31.0 | 29.1 |
| 19 | (CH$_2$Cl)$_2$/DMF (1%) | 20 mg | TMSOTf (100 μL) + HMDS (100 μL) | 85 | 60 min | 39.5 | 33.9 |
| 20 | (CH$_2$Cl)$_2$/tBuOH (1%) | 20 mg | TMSOTf (100 μL) + HMDS (100 μL) | 85 | 60 min | N | N |
| 21 | (CH$_2$Cl)$_2$ | 20 mg | TMSOTf (40 μL) + HMDS (100 μL) | 85 | 15 min | 9.2 | 8.1 |
| 22 | (CH$_2$Cl)$_2$ | 20 mg | TMSOTf (40 μL) + HMDS (100 μL) | 85 | 30 min | 17.1 | 18.6 |
| 23 | (CH$_2$Cl)$_2$ | 20 mg | TMSOTf (40 μL) + HMDS (100 μL) | 85 | 60 min | 17.4 | 23.4 |
| 24 | (CH$_2$Cl)$_2$ | 20 mg | TMSOTf (40 μL) + HMDS (100 μL) | 85 | 100 min | 18.3 | 24.1 |
| 25 | (CH$_2$Cl)$_2$ | 20 mg | TMSOTf (100 μL) + HMDS (100 μL) | 110 | 15 min | 37.4 | 38.1 |

The labeling yield was calculated based on HPLC results.
*Freshly synthesized precursor.
Unprotected uracil was used.

Reaction Temperature.

The reaction time could be significantly reduced by increasing the reaction temperature. The yield for FMAU could reach 38.1% within 15 min at 110° C. At this temperature, the α/β-anomer selectivity was decreased to 1:1.

Sugar (precursor 1).

Ten mg of sugar precursor provided slightly increased fluorination of the $^{18}$F-sugar yield as compared to 5 mg precursor. Therefore, 10 mg of sugar precursor was used for the reaction.

The estimated radiochemical yields for the radiofluorination step of the sugar precursor are the same for both the old and one-pot methods and according to certain embodiments is in the range of 30% to 40%.

Bis(trimethylsilyl)thymine (precursor 2).

In the automated synthesis system the applicants tested both the commercial precursor compounds, such as the 2,4-bistrimethylsilyl-5-methyluracil, and the one freshly prepared in house. Both in house made and commercially available bis(trimethylsilyl)thymine were used for the conjugation. The freshly prepared precursor did not help the reaction (Table 3, entry 10). The decreased yield for freshly prepared precursor 2 can be caused by the residue acetonitrile in the solvent, which is as result of the precursor preparation. However, the use of unprotected uracil (in situ protection) can also lead to the product but with lower yield (Table 3, entry 11). The applicants also tested different amounts of precursor 2 for the conjugation reactions (10, 20, 30, and 60 mg) and found that 20 mg was sufficient for the reaction.

Summary of Example 4.

Based on the results above, the finalized conditions for a one pot reaction for $^{18}$F-FMAU synthesis is as follows: Sugar fluorination was performed using $^{18}$F-TBAF or using $^{18}$F-KF/

$K_{222}$ system. Specifically, sugar precursor 1 (5~10 mg) was dissolved in 0.6 mL acetonitrile and added to an anhydrous $^{18}F$ source. The reaction mixture was heated at 80° C. for 15~20 min and the solvent was removed. TMSOTf (100-200 µL), HMDS (100 µL), and base precursor 2 (20 mg) was dissolved in dichloroethane (300 µL) and added to reaction vessel. Conjugation was performed at 80~85° C. for 60 min. After the solvent was removed under vacuum, KOMe (0.4 ml, ~3.0 N solution in MeOH) was added to the crude mixture and heated at 80° C. for 5-10 min. HCl (6.0 N, 0.2 ml) and 1.0 ml HPLC solvent (6% EtOH/buffer) were then added to the vessel to quench the reaction. The sample was then taken out for HPLC analysis/separation.

Example 5

Automated FMAU Production

Figure 2:
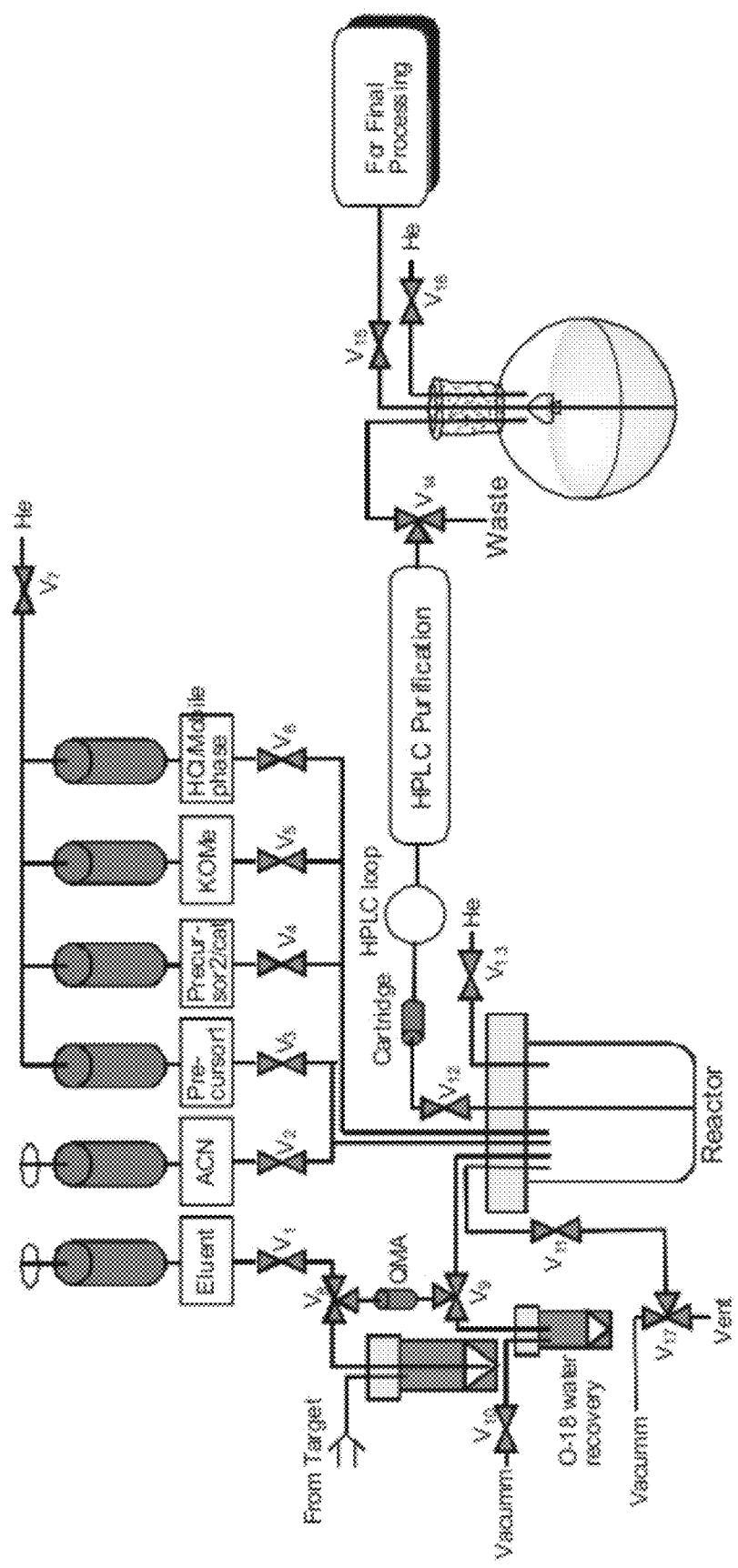
FIG. 2 is a schematic representation of the semi-automatic module for the radiosynthesis of $^{18}$F-FMAU.

Once the one pot conditions were discovered, the applicants then incorporated the method into an automated synthesis module as shown in FIG. 2. The module two way valves $V_1$-$V_6$ were used to control the solvent and reagent containing reservoirs 1-6. Reservoirs 3-6 were connected with a nitrogen or argon gas line. Reservoir 1 was connected with reactor through several control valves. The reactor was connected with vacuum pump, gas line, and the injection port of the HPLC system. In addition to valves 1-6, other valves, each controlling the appropriate operations as designated and necessary, such as transferring reagents or solvents, injection of the crude product to the HPLC, collection of fraction during HPLC purification and transfer of the final product from the collection flask to a receiving vial were used.

All reagents were stored in the reservoirs sequentially (FIG. 2) with the appropriate reagents and solvents under nitrogen prior to receiving the [$^{18}F$]-fluoride from the target of the cyclotron. After receiving the radioactivity into the synthesis module, radioactivity in $^{18}O$-water was then transferred from the receiving vial (FIG. 2, left bottom) to the ion exchange cartridge to trap the [$^{18}F$]-radioactivity, then eluted with $K_2CO_3$/$K_{222}$ or tetrabutylammonium bicarbonate (TBAB) from reservoir 1 into the reactor through V1, V8, V9, V11, and V17. Water and solvent were evaporated from the radioactive fluoride by heating at 95° C. and in combination with nitrogen flow and vacuum. The residual water was removed by azeotropic evaporation with acetonitrile transferred through V2, under vacuum and nitrogen flow. To the dry fluoride sugar triflate (precursor 1), acetonitrile (5-10 mg, 0.8 mL) was transferred through V3 and heated for 20 min at 85° C. The solvent was then evaporated and a dichloroethane (500 µL) solution of 2,4-bis-trimethylsilyl-5-ethyluracil (20 mg), HMDS (100 µL), and TMSOTf (150 µL) was added to the reactor through V4. The reaction mixture was heated for 1 h at 85° C. The solvent was then removed and KOMe solution was added through V5. The reactor was heated for 7 min at 80° C. and the solvent was removed under vacuum. The HCl and mobile phase solution was then added to the reactor and passed through a silica cartridge. The crude product solution was loaded on HPLC and the column was eluted with 8% EtOH/$Na_2HPO_4$ (50 mM, pH 6.5). The appropriate fraction was collected into the collection flask then transferred to the receiving vial after filtered through a Millipore filter. Rotavap was performed first if MeCN/water was used as the eluent. The product was co-injected with an authentic unlabeled sample onto an analytical column to confirm its identity and radiochemical purity.

Figure 3:
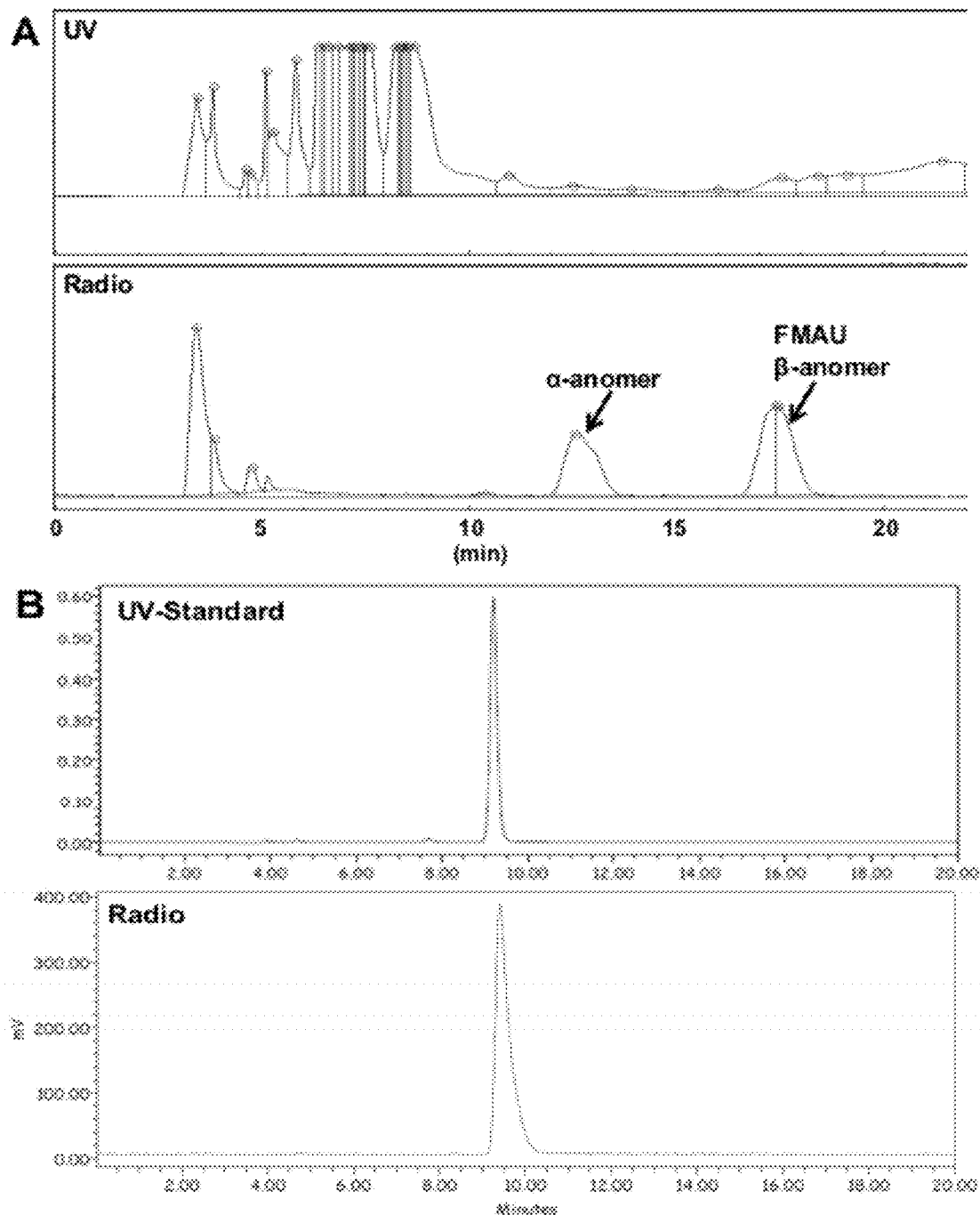
FIG. 3 (A) depicts HPLC-UV absorbance and ratio trace for FMAU purification and (B) depicts HPLC-UV absorbance of FMAU standard and the product radio-trace.

A representative HPLC trace of an automated synthesis, which started with 268 mCi of fluoride and produced 11 mCi of FMAU (Specific activity: 0.547 Ci/µmol) is shown in FIG. 3. The total synthesis time was approximately 150 min, and the α-anomer by-product was about 7.1 mCi.

Example 6

Microwave Assisted Conjugation

The use of microwave dielectric heating to reduce reaction times in organic transformations is rapidly increasing worldwide. The rate acceleration observed in microwave irradiation is due to material-wave interactions leading to thermal and/or non-thermal effects. Unlike conventional thermal heating methods, the microwave energy is transferred directly to the molecules (solvent, reactants, and catalysts) and converted into heat efficiently. Aside from the time gains compared with conventional heating methods, other advantages of microwave assisted reactions have been noted as, for example, cleaner reaction mixtures due to decreased sample decomposition and altered product distributions as well as improved chemical flexibility due to the ability to accelerate typically sluggish reactions of less activated substrates. Microwave assisted reactions have also been applied and demonstrated great potential in radiotracer preparation. According to certain embodiments, the use of microwave to increase radiolabeling yield, to reduce the sugar-base conjugation time, and to increase the α,β selectivity is also included. Microwave significantly enhanced the coupling efficiency of [$^{18}F$]-sugar and silylated uracil by reducing the reaction time to 15 min at 90 degrees celsius. The overall radiochemical yield was 20±4% (decay corrected, n=3). The α/β anomer ratio was 1:2.

Example 7

Microfluidic FMAU Production

Figure 4:
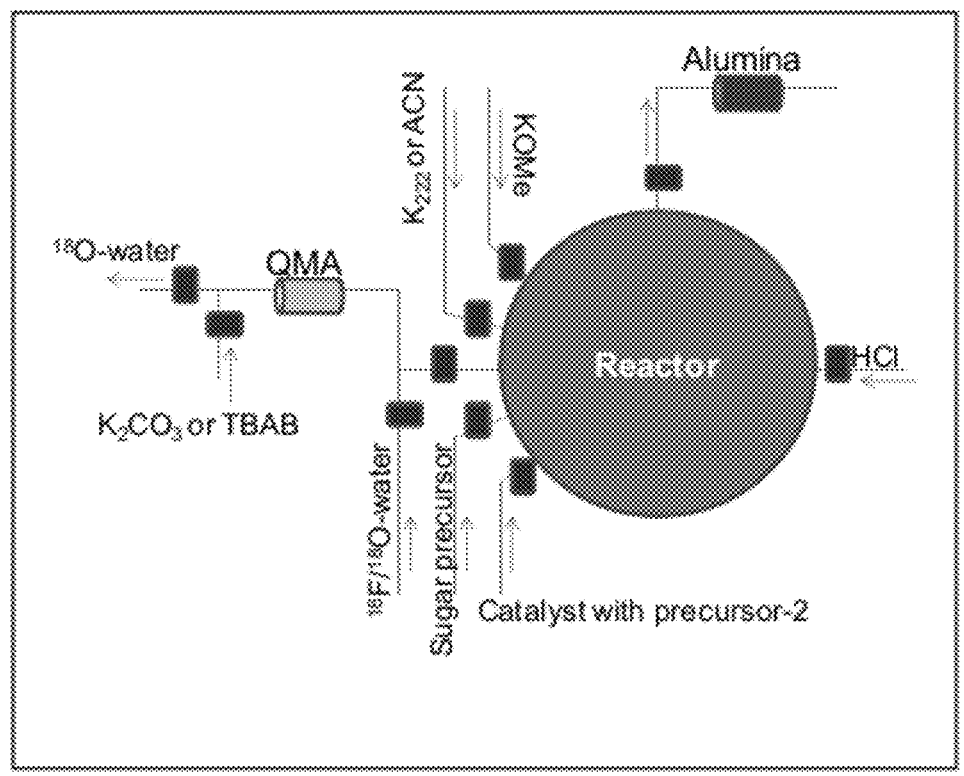
FIG. 4 is a schematic representation of coin-shaped microreactive chips for $^{18}$F-FMAU synthesis.
Figure 5:
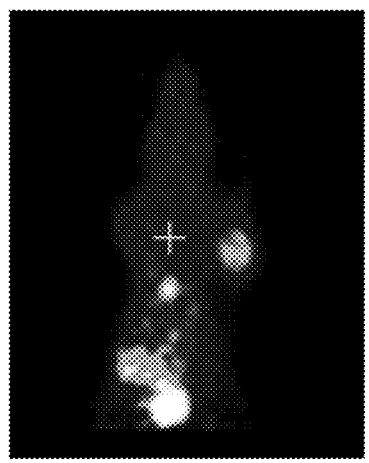
FIG. 5 depicts a representative FMAU image.

Microfluidic devices are known for several advantages that, if applied to the synthesis of radiopharmaceuticals, can circumvent many of the existing limitations and increase radiosynthesis output. In addition to the concentration advantage, these devices promise additional benefits derived from rapid mass and heat transfer. The newly developed synthetic method for $^{18}F$-FMAU can also be incorporated in a microfluidics chip for [$^{18}F$]F-FMAU synthesis. The general procedure for the fabrication of integrated, multilayer elastomeric microfluidic chips has been described in the literature. According to the current invention, users can trap the F-18 in a QMA cartridge, which is washed on the microfluidic reactor with $K_2CO_3$ or t-butyl ammonium bicarbonate (TBAB) (FIG. 4). The acetonitrile solution of Kriptofix 222 ($K_{222}$, used with $K_2CO_3$ condition) or pure acetonitrile solution (used with TBAB condition) is added to make the fluoride ion dry. The FMAU sugar precursor is added and the reaction is performed at a temperature ranging from 70-110° C. After the reaction is done, the solvent is removed and the catalyst with the second precursor is added to the reactor. After conjugation, KOMe is added for deprotection and HCl is used to neutralize the crude mixture. HPLC purification is performed to separate the final product.

Example 8

Other 5-Substituted Thymidine Analogue Production

The newly developed method can be easily extended for the synthesis of other [$^{18}F$]-labeled thymidine and cytidine analogs and can be adapted for full automation. Examples are listed in Table 4.

TABLE 4

Other 5-substituted thymidine analogue production.

| Entry | solvent | silylated uracil | Catalyst | T (°C.) | Time | α-anomer | β-anomer |
|---|---|---|---|---|---|---|---|
| FAU | ACN | 20 mg | TMSOTf(100 μL)/HMDS(100 μL) | 80 | 60 min | 21.8 ± 2.6 | 16.3 ± 3.0 |
| FEAU | Same | Same | Same | Same | Same | 14.8 ± 3.7 | 9.1 ± 2.4 |
| FFAU | Same | Same | Same | Same | Same | 17.0 ± 0.6 | 16.5 ± 0.5 |
| FCAU | Same | Same | Same | Same | Same | 38.5 ± 10.1 | 29.3 ± 5.1 |
| FBAU | Same | Same | Same | Same | Same | 33.3 ± 14.6 | 23.0 ± 8.7 |
| FIAU | Same | Same | Same | Same | Same | 36.5 ± 4.7 | 29.3 ± 0.3 |

The overall radiochemical yield in the automated synthesis was 12±3% (decay corrected) with 547 mCi/μmol specific activity. The α/β anomer ratio was 4:6. The overall reaction time was about 150 min from the end of bombardment. This yield was only slightly lower than the previous synthesis yields (15-20%) from the old method. However, the present one-pot method simplified the reaction procedures and reduced the total production time, making the non-decay-corrected yield comparable to the old method.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

All patent and literature references cited in the present specification are hereby incorporated by reference in their entirety.

REFERENCES

1. Mangner, T. J.; Klecker, R. W.; Anderson, L.; Shields, A. F. *Nucl Med Biol* 2003, 30, 215-24.
2. Alauddin, M. M.; Conti, P. S.; Fissekis, J. D. *J. Labelled. Comp. Radiopharm.* 2002, 45, 583-590.
3. Alauddin, M. M.; Conti, P. S.; Fissekis, J. D. *J. Labelled. Comp. Radiopharm.* 2003, 46, 285-289.
4. Kappe, C. O.; Dallinger, D. *Mol Divers* 2009, 13, 71-193.
5. Santagada, V.; Frecentese, F.; Perissutti, E.; Fiorino, F.; Severino, B.; Caliendo, G. *Mini Rev Med Chem* 2009, 9, 340-58.
6. Stone-Elander, S.; Elander, N.; Thorell, J. O.; Fredriksson, A. *Ernst Schering Res Found Workshop* 2007, 243-69.
7. Elizarov, A. M.; van Dam, R. M.; Shin, Y. S.; Kolb, H. C.; Padgett, H. C.; Stout, D.; Shu, J.; Huang, J.; Daridon, A.; Heath, J. R. *J Nucl Med* 2010, 51, 282-7.
8. Duffy, D. C.; McDonald, J. C.; Schueller, J. A.; Whitesides, G. M. *Analytical Chemistry* 1998, 70, 4974-4984.

What is claimed is:

1. A method of synthesizing 2'-deoxy-2'-[$^{18}$F]-fluoro-5-substituted-1-β-D-arabinofuranosyl-uracil or -cytosine compounds in a one-pot reaction comprising:
    a) radiolabeling a precursor sugar with $^{18}$F;
    b) contacting the $^{18}$F radiolabeled sugar with a silylated uracil or cytosine in the presence of trimethylsilyl trifluorosulfonate (TMS-O-Tf) and hexamethyldisilazane (HMDS);
    c) incubating the components in step (b) under conditions which allow for conjugation of the $^{18}$F radiolabeled sugar and the silylated uracil or cytosine;
    d) removing the protecting groups of the components in step (c); and
    e) purifying the deprotected product.

2. The method according to claim 1, wherein the 2'-deoxy-2'-[$^{18}$F]-fluoro-5-substituted-1-β-D-arabinofuranosyl-uracil is 2'-deoxy-2'-[$^{18}$F]fluoro-5-methyl-1-β-D-arabinofuranosyl-uracil ([$^{18}$F]-FMAU).

3. A method for the fully automated synthesis of [$^{18}$F]-FMAU comprising the method of claim 1, wherein synthesis takes place in a fully automated cGMP-compliant radiosynthesis module.

4. A method of synthesizing an [$^{18}$F]-labeled 2'-deoxy-arabino 5-substituted or unsubstituted uracil or cytosine nucleoside in a one-pot reaction comprising:
    a) radiolabeling a precursor sugar with $^{18}$F;
    b) contacting the $^{18}$F radiolabeled sugar with a silylated uracil or cytosine in the presence of trimethylsilyl trifluorosulfonate (TMS-O-TO and hexamethyldisilazane (HMDS);
    c) incubating the components in step (b) under conditions which allow for conjugation of the $^{18}$F radiolabeled sugar and the silylated uracil or cytosine derivatives;
    d) removing the protecting groups of the components in step (c); and
    e) purifying the deprotected product.

5. The method according to claim 4, wherein the [$^{18}$F]-labeled 2'-deoxy-arabino 5-substituted or unsubstituted uracil or cytosine nucleoside is selected from the group consisting of 2'-fluoro-5-ethyl-1-β-D-arabinofuranosyluracil (FEAU), 2'-Deoxy-2'-fluoro-5-fluoro-1-β-D-arabinofuranosyluracil (FFAU), 1-(2-deoxy-2-fluoro-β-D-arabinofuranosyl)-5-chlorouracil (FCAU), 1-(2-deoxy-2-fluoro-β-D-arabinofuranosyl)-5-bromouracil (FBAU), 1-(2-deoxy-2-fluoro-(3-D-arabinofuranosyl)uracil (FAU), 2'-fluoro-2'-deoxy-1-β-D-arabinofuranosyl-5-iodouracil (FIAU), 1-(2-deoxy-2-fluoro-β-D-arabinofuranosyl)cytosine (FAC), 2'-deoxy-2'-fluoro-5-methyl-1-β-D-arabinofuranosylcytosine (FMAC), 2'-fluoro-5-ethyl-1-β-D-arabinofuranosylcytosine (FEAC), 2'-Deoxy-2'-fluoro-5-fluoro-1-β-D-arabinofuranosyluracil (FFAC), 1-(2-deoxy-2-fluoro-β-D-arabinofuranosyl)-5-chlorocytosine (FCAC), 1-(2-deoxy-2-fluoro-β-D-arabinofuranosyl)-5-bromocytosine (FBAC), and 2'-deoxy-2'-fluoro-5-hydroxymethyl-1-β-D-arabinofuranosylcytosine (FHMAC).

6. A method for fully automated synthesis [$^{18}$F]-labeled thymidine or cytidine analogues comprising the method of claim 4, wherein synthesis takes place in a fully automated cGMP-compliant radiosynthesis module.

7. A method of synthesizing 2'-deoxy-2'-[$^{18}$F]-fluoro-5-substituted-1-β-D-arabinofuranosyl-uracil or -cytosine compounds in a one-pot reaction comprising:
   a) radiolabeling a precursor sugar with $^{18}$F;
   b) filtering the $^{18}$F radiolabeled sugar produced in step (a) through a cartridge;
   c) contacting the $^{18}$F radiolabeled sugar with a silylated uracil or cytosine in the presence of a Friedel-Crafts catalyst;
   d) incubating the components in step (c) under conditions which allow for conjugation of the $^{18}$F radiolabeled sugar and the silylated uracil or cytosine;
   e) incubating the components in step (d) under conditions which allow for removal of the protecting groups of the components in step (d) thereby removing the protecting groups of the components in step (d); and
   f) purifying the deprotected product.

* * * * *